United States Patent [19]

Hickmann

[11] 4,169,478
[45] Oct. 2, 1979

[54] SURGICAL HEAD CLAMP

[75] Inventor: Horst R. Hickmann, Anderson Township, Hamilton County, Ohio

[73] Assignee: Ohio Medical Instrument Company, Inc., Cincinnati, Ohio

[21] Appl. No.: 886,730

[22] Filed: Mar. 15, 1978

[51] Int. Cl.[2] .............................................. A61B 19/00
[52] U.S. Cl. .................................... 128/346; 269/328; 403/59
[58] Field of Search ............... 128/346, 303 R, 303 B; 403/59, 60; 248/176, 309 A; 269/328; 27/13

[56] References Cited

U.S. PATENT DOCUMENTS

| | | | |
|---|---|---|---|
| 2,966,383 | 12/1960 | Boetcker et al. | 269/328 |
| 3,099,441 | 7/1963 | Ries | 269/328 |
| 3,835,861 | 9/1974 | Kees, Jr. et al. | 128/346 |
| 4,108,426 | 8/1978 | Lindstroem et al. | 269/328 |

*Primary Examiner*—Stephen C. Pellegrino
*Attorney, Agent, or Firm*—James W. Pearce; Roy F. Schaeperklaus

[57] ABSTRACT

A surgical head clamp which comprises a framework on which a first head engaging pin member and a rotatable bracket are supported. The axis of the first pin member is the axis of rotation of the bracket. Spaced second and third head engaging pin members are mounted on the bracket and directed toward the first pin member. The first pin member can be advanced axially toward the bracket to cause the pin members to engage the head. The bracket can be locked in selected position and is releaseable to permit turning of the head about said axis without releasing the pin members from the head.

5 Claims, 22 Drawing Figures

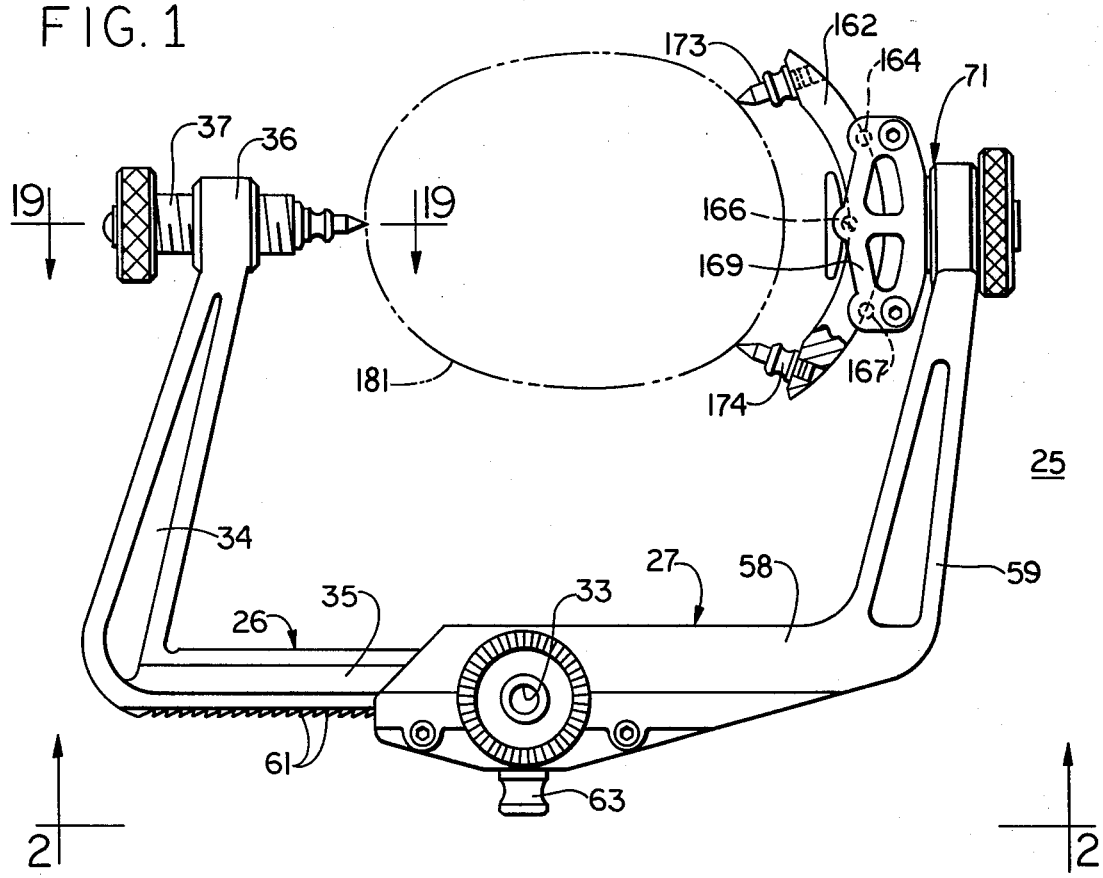
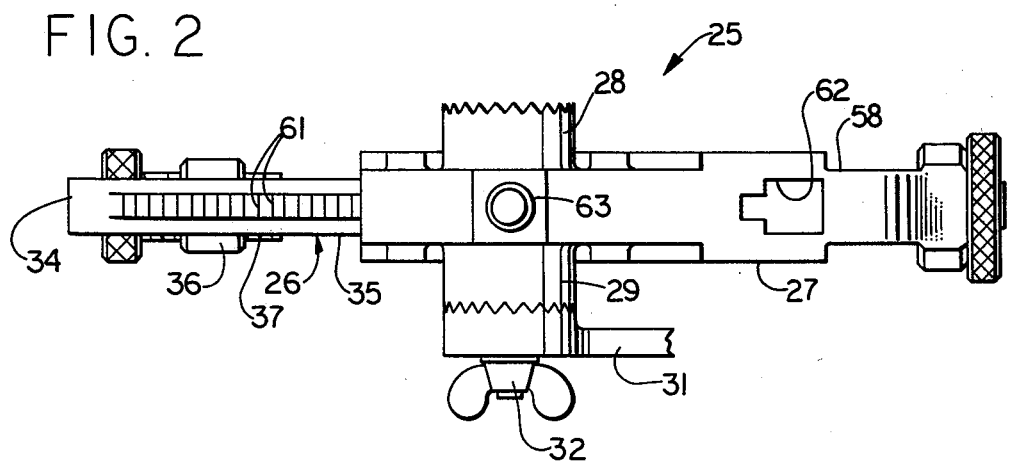

SURGICAL HEAD CLAMP

This invention relates to a surgical clamp. More particularly, this invention relates to a head holding clamp for use in surgical operations. This invention further relates to an improvement in head holding clamps of the type shown in Kees and Hickman U.S. Pat. No. 3,835,861.

In the performance of an operation on the head of a patient, it is necessary that the head be held firmly in position. However, it may be necessary to turn the head during the operation to improve drainage or to permit better access to portions of the head. An object of this invention is to provide a head clamp which firmly holds a head but which can be released to permit turning of the head.

A further object of this invention is to provide such a clamp which permits turning of a head without release of pin portions thereof which directly engage the head.

Briefly, this invention provides a surgical head clamp in which a head is held by pins or the like at three spaced positions. One of the pins is carried by a carrier which can exert pressure on that one of the pins axially thereof. The other pins are carried by a bracket which can swing about an axis aligned with the axis of the first pin. A latch can lock the bracket against turning or can be actuated to release the bracket so that the head can be turned with relation to the frame-work of the clamp to alter the position of the head.

The above and other objects and features of the invention will be apparent to those skilled in the art to which this invention relates from the following detailed description and the drawings, in which:

FIG. 1 is a plan view of a surgical head clamp constructed in accordance with an embodiment of this invention, a head being shown in double-dot-dash lines in association therewith;

Figure 3:
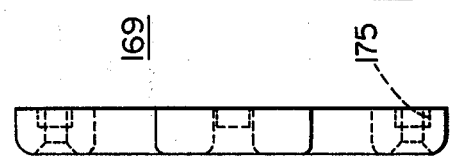
Figure 4:
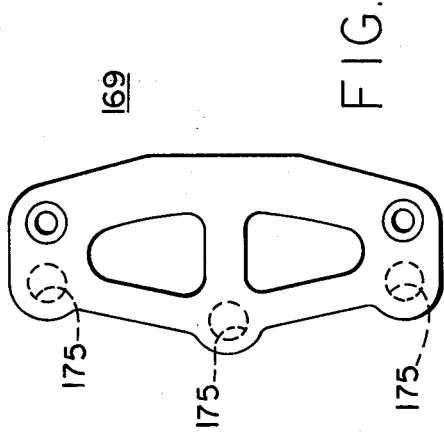
Figure 2A:
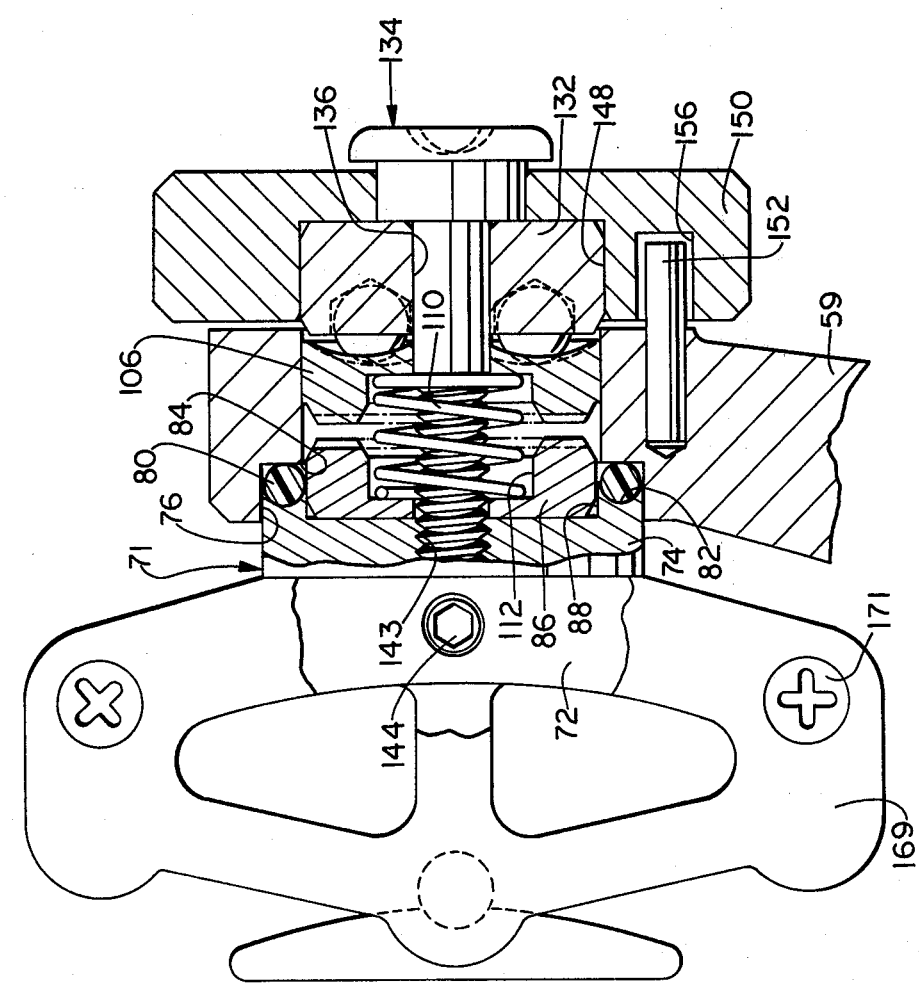
FIG. 2 is a view in side elevation thereof looking in the direction of the arrows 2—2 in FIG. 1, a portion of a support bracket being shown in association therewith.
Figure 5:
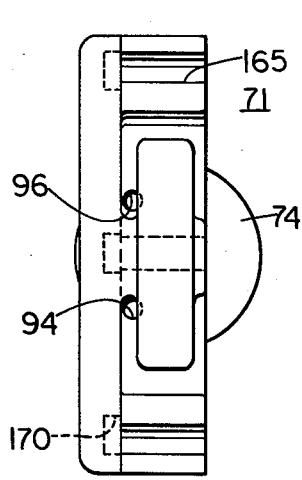
Figure 6:
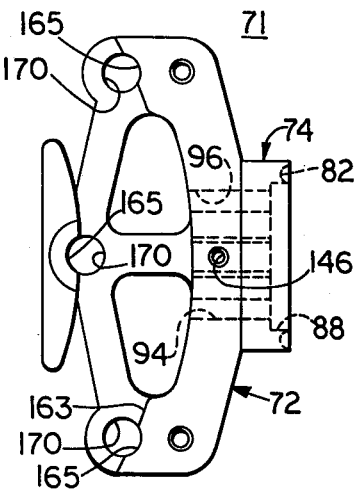
Figure 7:
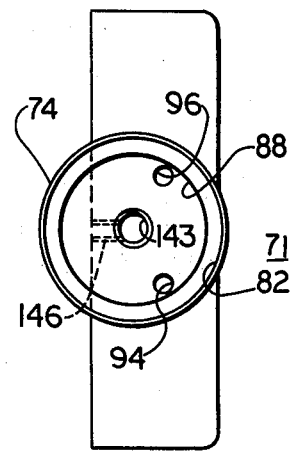
Figure 8:
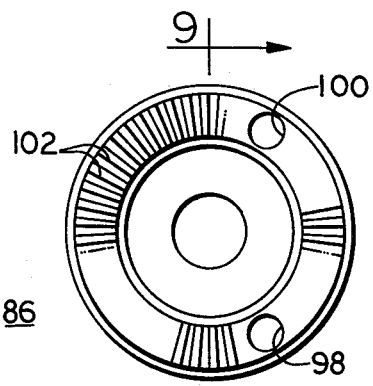
Figure 9:
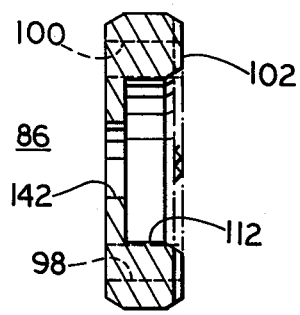
Figure 10:
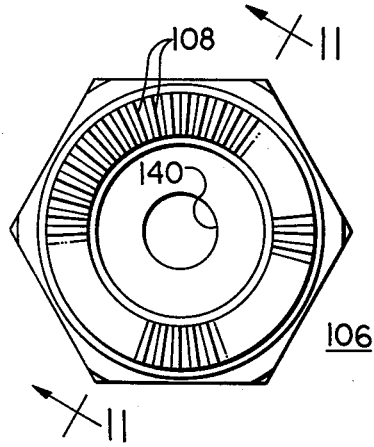
Figure 11:
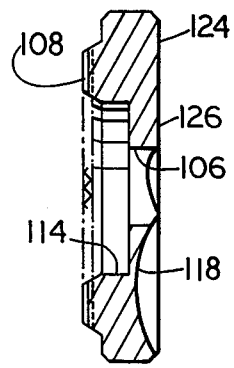
Figure 12:
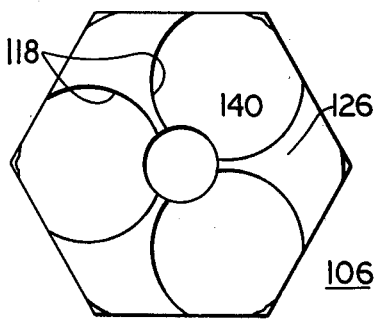
Figure 13:
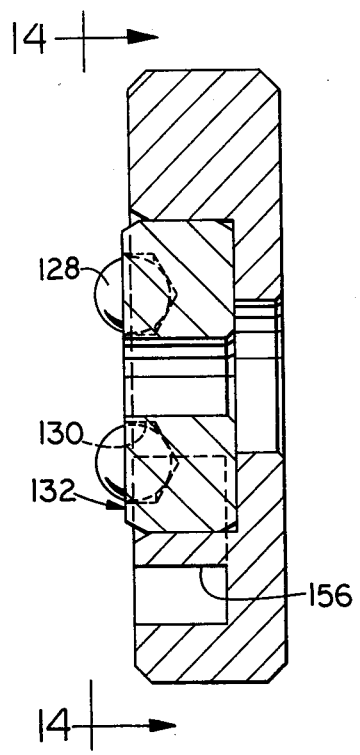
Figure 14:
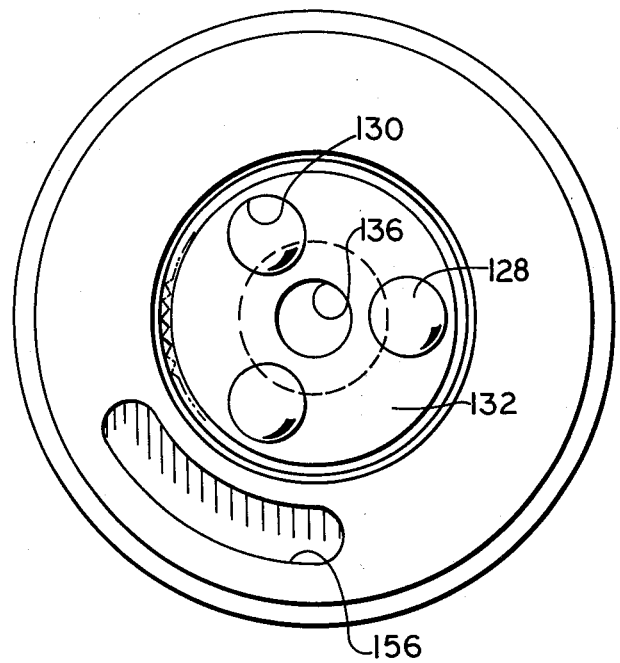
Figure 15:
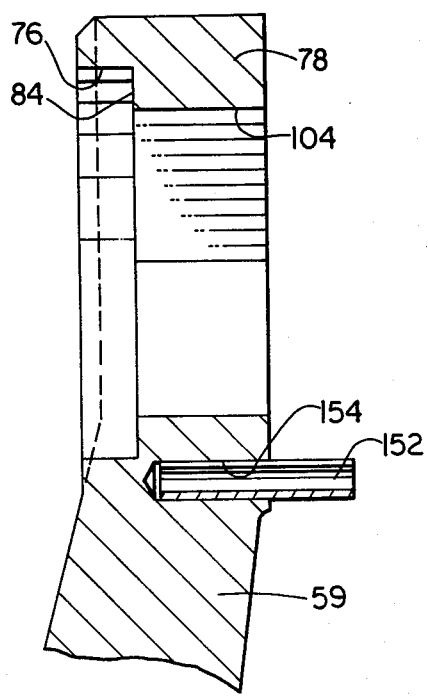
Figure 16:
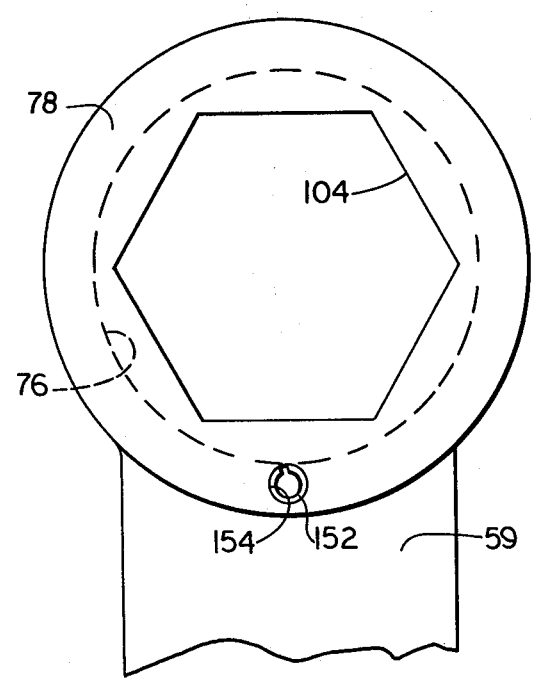
Figure 18:
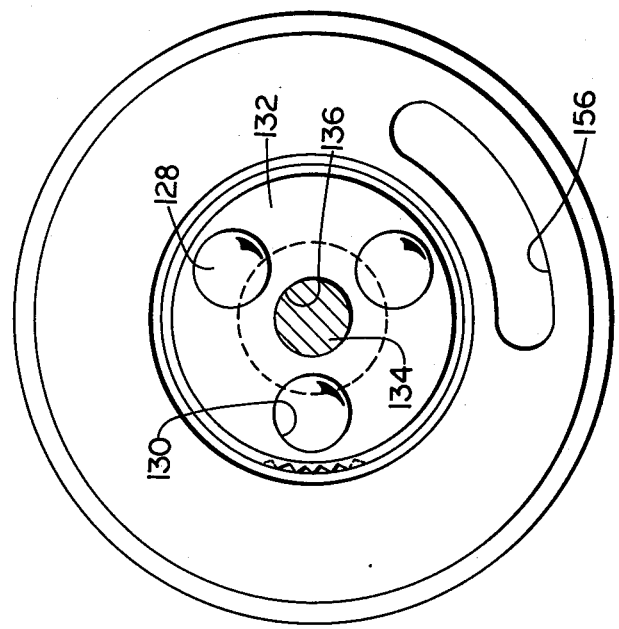
Figure 17:
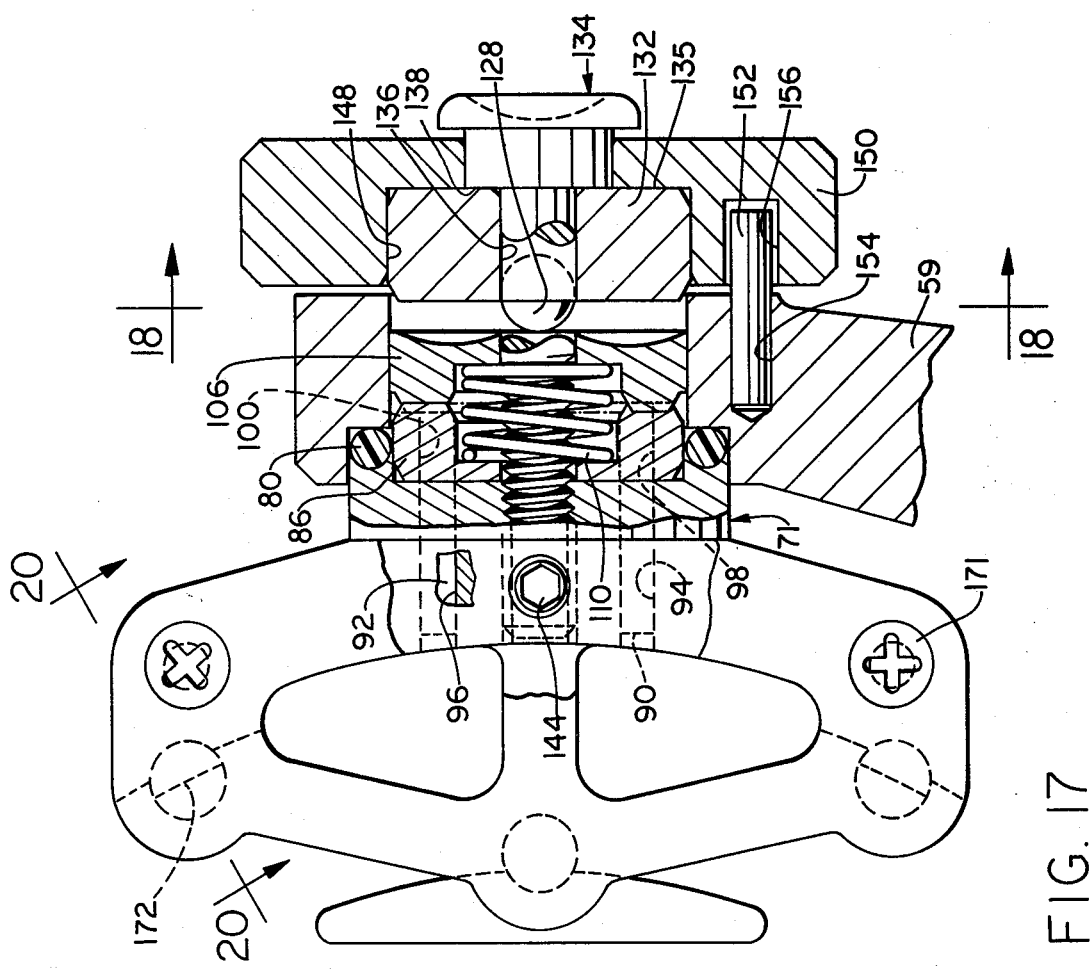
Figure 19:
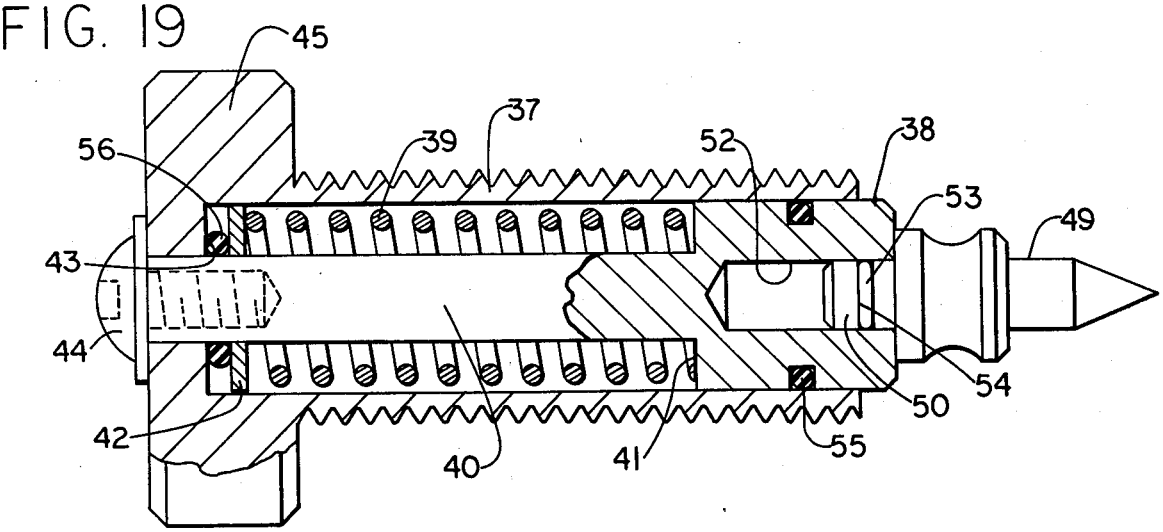
Figure 20:
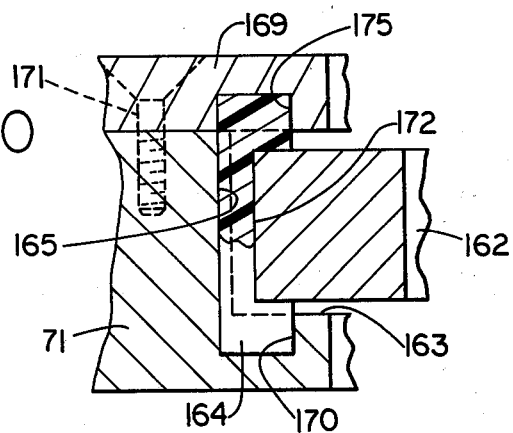

FIG. 2A in an enlarged view partly in plan and partly in section of a locking bracket and supports therefor of the head clamp shown in FIG. 1 the bracket being shown in released position;

FIG. 3 is a plan view of a cover plate of the bracket shown in FIG. 2A;

FIG. 4 is a view in side elevation of the cover plate shown in FIG. 3;

FIG. 5 is a view in end elevation of a body of the bracket shown in FIG. 2A;

FIG. 6 is a plan view of the bracket body shown in FIGS. 2A and 5;

FIG. 7 is another view in end elevation of the bracket body shown in FIGS. 2A, 5 and 6;

FIG. 8 is a view in end elevation of a stop ring which is a part of the bracket;

FIG. 9 is a view in section taken on the line 9—9 in FIG. 8;

FIG. 10 is a view in end elevation of a sliding stop member of the head clamp;

FIG. 11 is a view in section taken on line 11—11 in FIG. 10;

FIG. 12 is another view in end elevation of the sliding stop ring;

FIG. 13 is a view in section of an operating handle assembly of the head clamp, ball members being shown in association therewith;

FIG. 14 is a view in end elevation of the operating handle assembly and ball members looking in the direction of the arrows 14—14 in FIG. 13;

FIG. 15 is a view in section of a head portion of a frame of the head clamp;

FIG. 16 is a view in end elevation of the head portion of the frame of the head clamp shown in FIG. 15;

FIG. 17 is a view partly in plan and partly in section of the locking bracket and supports therefor in locked position;

FIG. 18 is a view in end elevation of the operating handle assembly and ball members looking in the direction of the arrows 18—18 in FIG. 17;

FIG. 19 is a view in section taken on an enlarged scale on the line 19—19 in FIG. 1;

FIG. 20 is a view in section taken on the line 20—20 in FIG. 17; and

Figure 21:
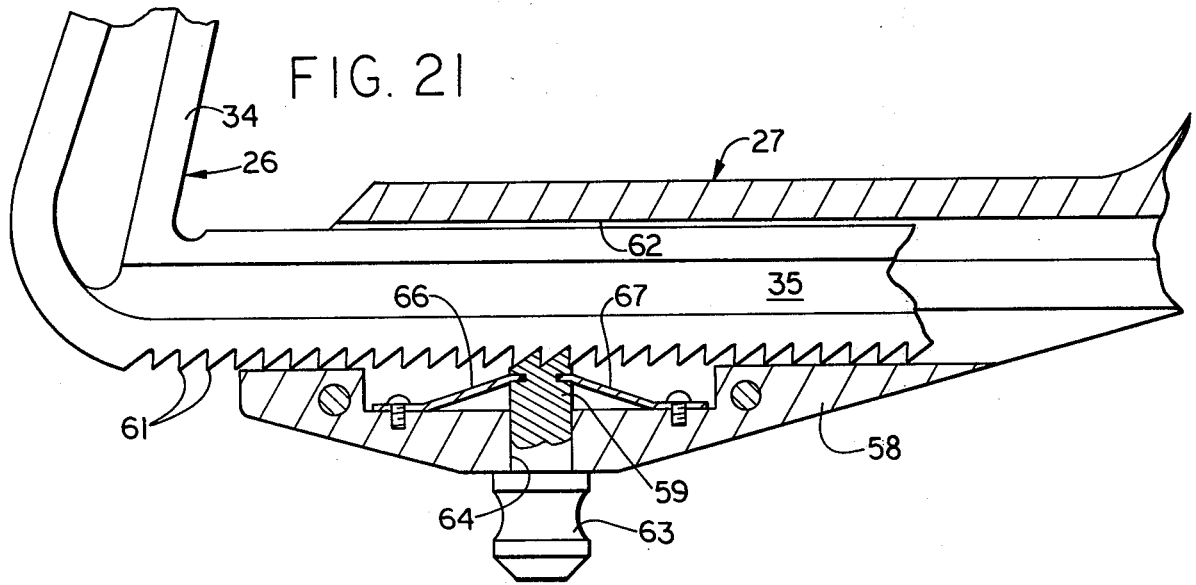

FIG. 21 is a sectional view through main sections of the head clamp.

In the following detailed description and the drawings, like reference characters indicate like parts.

In FIGS. 1 and 2 is shown a surgical head clamp 25 constructed in accordance with an embodiment of this invention. The head clamp 25 includes main sections 26 and 27, each of which is of generally L-shape. On sides of the main section 27, are disposed clamping bosses 28 and 29 to either of which a support or mount 31 can be attached to support the clamp 25. A thumb screw 32 can be received in a threaded socket 33 in one of the bosses to attach the main section 27 to the support 31.

The main section 26 includes a first arm 34 having an internally threaded boss 36 at one end thereof and a second arm 35. A pin carrier 37 is threaded in the boss 36. The pin carrier 37 is hollow as shown in FIG. 19, and a plunger 38 is mounted for movement to the right and left inside the pin carrier 37. A compression spring 39 surrounds a shank 40 of the plunger 38 and bears on a shoulder 41 of the plunger 38 and on a washer 42. The washer 42 engages an O-ring seal 56 which, in turn, engages an interior flange or shoulder 43 of the pin carrier 37. A screw fastener 44 mounted in the plunger 38 and engageable with a head portion 45 of the pin carrier 37 limits movement of the plunger 38 to the right as shown in FIG. 19. A pin member 49 is mounted on the plunger 38. A shank 50 of the pin member 49 is received in a socket 52 in the plunger 38. An O-ring 53 mounted in a circumferential slot 54 in the shank 50 holds the pin member 49 in position in the plunger socket 52. An O-ring seal 55 mounted on the plunger 38 and the O-ring seal 56 form seals between the plunger 38 and the pin carrier 37 surrounding the spring 39.

The main section 27 includes a first arm 58 and a second arm 59. The arm 35 of the section 26 carries rack teeth 61 (FIGS. 1 and 2). The arm 35 is slideably and telescopically received inside an elongated opening 62 (FIG. 21) in the first arm 58 of the section 27. A pawl 63 is slideably mounted in an opening 64 (FIG. 21) in the arm 58 for movement transversely of the direction of movement of the arm 35. Teeth of the pawl 63 can engage the rack teeth 61 to hold the arms 35 and 58 against movement in a direction to cause separation of the arms 34 and 59. Leaf springs 66 and 67 attached to the arm 58 urge the pawl 63 to the latched position shown in FIG. 21. However, the pawl 63 can be withdrawn to release the teeth permitting movement of the arms 34 and 59 away from each other. The rack teeth are constructed to restrain movement of the arms 34 and 59 of the main sections away from each other but to permit movement toward each other.

The second arm 59 of the main section 37 supports a locking bracket 71. The locking bracket 71 includes a body 72 (FIG. 2A) carried by an integral head 74, which is received in a cylindrical socket 76 in a boss 78 at a free end of the main section arm 59. A resilient bearing ring 80 is received in an annular slot 82 in the head 74 and engages a shoulder 84 at the base of the socket 76. The bearing ring 80 can be of the material known as Teflon, a trademark of E. I. D. duPont de Nemours & Co.

A stop ring 86 is received in a socket 88 in the head 74 and is held in assembled relation with the body 72 by roll pins 90 and 92 (FIG. 17) received in bores 94 and 96 in the bracket 71 and bores 98 and 100 in the stop ring 86, respectively. The stop ring 86 can be formed of hard, wear resistant metal such as stainless steel and carries a ring of teeth 102 (FIGS. 8 and 9).

A hexagonal socket 104 is provided in the boss 78 in coaxial relation with the cylindrical socket 76. A generally hexagonal sliding stop member 106 can slide lengthwise of the hexagonal socket 104 (to the right and left in FIGS. 2A and 17). As shown in FIGS. 10 and 11, the sliding stop member 106 is provided with a ring of teeth 108, which can engage the teeth 102 of the stop ring 86. The sliding stop member 106 can also be formed of hard wear resistant metal such as stainless steel. A compression spring 110 urges the sliding stop member 106 to the FIG. 2A position at which the teeth 102 and 108 are disengaged. The compression spring 110 is mounted in sockets 112 and 114 in the stop ring 86 and the sliding stop member 106, respectively. The sliding stop member 106 is provided with a set of three dished sockets 118 on an outer face 124 thereof, lands 126 are provided between the sockets 118.

The sliding stop member 106 is advanced to the FIG. 17 position by action of a set of ball actuators 128 (FIGS. 13 and 14), which are received in sockets 130 in an actuator disc 132. The actuator disc 132 is rotatably mounted on a pivot bolt member 134 (FIG. 17) which passes through a bearing opening 136 centrally of the actuator disc 132. A shoulder 138 on the pivot bolt member 134 engages an outer face 135 of the actuator disc 132. The pivot bolt member 134 extends through clear bores 140 and 142 in the sliding stop member 106 and the stop ring 86, respectively, and is threaded in a bore 143 in the bracket 71. A set screw 144 threaded in a transverse bore 146 in the bracket 71 locks the pivot bolt member 134 in position. The actuator disc 132 can be formed of hard wear resistant metal such as stainless steel and is received and tightly held in a socket 148 in a handle disc 150.

The handle disc 150 together with the actuator disc 132 can be turned from the FIG. 2A position at which the ball actuators 128 are located in the dished sockets 118 to the FIG. 17 position, at which the ball actuators 128 are located on the lands 126 and the teeth of the sliding stop member 106 and the stop ring 86 are in engagement to prevent turning of the bracket 71. A roll pin 152 mounted in a socket 154 in the main section arm 59 extends into an arcuate slot 156 in the handle disc 150 to limit swinging of the handle disc 150.

The bracket 71 supports an arcuate bar 162 for sliding movement as shown in FIG. 1. The arcuate bar 162 is received in a slot 163 (FIG. 20) in the bracket 71. Guide pins 164, 166 and 167 are mounted in slots 165 (one of which is shown in FIG. 20) in the bracket 71 and are held in position therein by a plate 169 attached to the bracket 71 by fasteners 171. Sockets 170 in the bracket 71 and sockets 175 in the plate 169 receive end portions of the guide pins 164, 166, and 167. The guide pin 164 is provided with a slot 172 in which the arcuate bar 162 is slidably received. The other guide pins are provided with similar slots in which the arcuate bar 162 is slidably received. The guide pins 164, 166 and 167 can be formed of plastic resin commonly called Nylon or other suitable bearing material. Head engaging pin members 173 and 174 are mounted adjacent opposite ends of the arcuate bar 162 and are directed toward the pin member 49. The pin members 173 and 174 can be similar in construction to the pin member 49 already described.

When the head clamp 25 is to be used, the handle disc 150 is positioned with the ball actuators 128 on the lands 126 so that the bracket 71 is locked against turning. The section 26 is withdrawn to the left as shown in FIG. 1 to provide space for a head 181 between the pin member 49 and the pin members 173 and 174 carried by the arcuate arm 162. The sections 26 and 27 can then be brought together to bring the pin members to the sides of the head. Then the pin carrier 37 is turned to advance the pin member 49 and cause all of the pin members to advance to the depth required to hold the head 181 in a selected position and to cause the bracket 71 to be urged to the right as shown in FIG. 17 to hold the bearing ring 80 against the shoulder 84. The arcuate bar 162 can slide back and forth to adjust for irregularities in the head 181 and for the position of the pin members on the head. As operative procedures are conducted, it can be necessary to turn the head to permit drainage of fluids or for other reasons. The handle disc 150 can be turned to its other position so that the ball actuators 128 are received in the dished sockets 118 without releasing the pin members 49, 173 and 174 from the head 181. The axis of the pin carrier 37 is aligned with the axis of turning of the bracket 71 so that, when the teeth of the sliding stop member 106 and the stop ring 86 are released, the head 181 can be turned about that axis without release of the pin members. When the head has been repositioned, the handle disc can be returned to the locked position, and the head 181 is again firmly locked in adjusted position.

The surgical clamp head structure illustrated in the drawings and described above is subject to structural modification without departing from the spirit and scope of the appended claims.

Having described my invention, what I claim as new and desire to secure by Letters Patent is:

1. A surgical head clamp which comprises a framework, means for supporting the framework, a first head engaging pin means supported on the framework, a bracket rotatably supported on the framework aligned with and spaced from the first head engaging pin means, spaced second and third head engaging pin means mounted on the bracket, means for advancing the first head engaging pin means axially toward the bracket to cause the head engaging pin means to engage the head, the first head engaging pin means being aligned with the axis of rotation of the bracket, and means for releaseably locking the bracket in selected position, the bracket being releaseable to permit turning of the head about said axis without releasing the head engaging pin means from the head.

2. A surgical head clamp as in claim 1 in which the means for advancing the first head engaging pin means resiliently urges the first head engaging pin means toward the bracket, the framework includes a bearing face opposed to the bracket and extending transversely of the axis of turning of the bracket, and the surgical head clamp includes a bearing ring interposed between said bearing face and the bracket against which the bracket is resiliently urged.

3. A surgical head clamp as in claim 1 in which the means for releaseably locking the bracket includes teeth carried by the bracket and directed outwardly thereof, a toothed sliding stop member slideably mounted on the framework for sliding toward and away from bracket, and means for advancing the sliding stop member between a locking position in which teeth carried by the locking stop member engage the teeth carried by the bracket and a released position in which the bracket is free to turn.

4. A surgical head clamp as in claim 3 in which the means for advancing the sliding stop member includes spring means urging the sliding stop member to released position, a handle disc rotatably mounted on the bracket, and a plurality of angularly spaced actuator projections on the handle disc engaging an outer face of the sliding stop member, the outer face of the sliding stop member includes a plurality of dished sockets receiving the actuator projections when the sliding stop member is in released position, and turning of the handle disc causes advance of the actuator projections along sides of the dished sockets to advance the sliding stop member to locking position.

5. A surgical head clamp as in claim 4 in which the outer face of the sliding stop member includes lands between the dished sockets and the actuator projections ride on the lands when the sliding stop member is in locking position.

* * * * *